United States Patent
Fuchigami

(10) Patent No.: US 11,049,251 B2
(45) Date of Patent: Jun. 29, 2021

(54) APPARATUS, METHOD, AND PROGRAM FOR LEARNING DISCRIMINATOR DISCRIMINATING INFARCTION REGION, DISCRIMINATOR FOR DISCRIMINATING INFARCTION REGION, AND APPARATUS, METHOD, AND PROGRAM FOR DISCRIMINATING INFARCTION REGION

(71) Applicant: FUJIFILM Corporation, Tokyo (JP)

(72) Inventor: Takuya Fuchigami, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 88 days.

(21) Appl. No.: 16/536,242

(22) Filed: Aug. 8, 2019

(65) Prior Publication Data

US 2020/0074633 A1 Mar. 5, 2020

(30) Foreign Application Priority Data

Aug. 31, 2018 (JP) .............................. JP2018-162861

(51) Int. Cl.
*A61B 5/00* (2006.01)
*A61B 5/055* (2006.01)
(Continued)

(52) U.S. Cl.
CPC .......... *G06T 7/0016* (2013.01); *A61B 5/0042* (2013.01); *A61B 5/055* (2013.01);
(Continued)

(58) Field of Classification Search
None
See application file for complete search history.

(56) References Cited

U.S. PATENT DOCUMENTS 10,373,718 B2 * 8/2019 Menon .................... G16H 50/20
10,395,762 B1 * 8/2019 Fram ...................... G16H 30/40
(Continued)

FOREIGN PATENT DOCUMENTS

| JP | 2013-165765 A | 8/2013 |
| JP | 2014-518516 A | 7/2014 |
| WO | 2009/148041 A1 | 12/2009 |

OTHER PUBLICATIONS

Karonen et al., "Combined Diffusion and Perfusion MRI With Correlation to Single-Photon Emission CT in Acute Ischemic Stroke," Stroke, Aug. 1999;30(8):1583-90. doi: 10.1161/01.str.30.8.1583 (Year: 1999).*

(Continued)

*Primary Examiner* — Soo Shin
(74) *Attorney, Agent, or Firm* — Studebaker & Brackett PC

(57) ABSTRACT

An image acquisition unit acquires a CT image and one or more MRI images of the brain of a subject that has developed a cerebral infarction. An infarction region extraction unit extracts an infarction region corresponding to the time elapsed since the development from the MRI image. A registration unit performs registration between the CT image and the MRI image. An infarction region specification unit specifies the infarction region corresponding to the time elapsed since the development in the CT image on the basis of the result of the registration. A learning unit learns a discriminator which discriminates an infarction region corresponding to the time elapsed since the development in the CT image to be discriminated, using the infarction region corresponding to the time elapsed since the development, which has been specified in the CT image, as teacher data.

10 Claims, 6 Drawing Sheets

(51) Int. Cl.

| | | |
|---|---|---|
| *A61B 6/00* | (2006.01) | |
| *A61B 6/03* | (2006.01) | |
| *G01R 33/48* | (2006.01) | |
| *G01R 33/50* | (2006.01) | |
| *G06N 20/00* | (2019.01) | |
| *G06T 7/00* | (2017.01) | |
| *G06T 7/30* | (2017.01) | |
| *G06T 7/33* | (2017.01) | |
| *G16H 20/10* | (2018.01) | |
| *G16H 30/40* | (2018.01) | |
| *G16H 40/63* | (2018.01) | |
| *G16H 50/20* | (2018.01) | |

(52) U.S. Cl.
CPC .............. *A61B 6/032* (2013.01); *A61B 6/501* (2013.01); *A61B 6/5247* (2013.01); *A61B 6/54* (2013.01); *G01R 33/4806* (2013.01); *G01R 33/50* (2013.01); *G06N 20/00* (2019.01); *G06T 7/30* (2017.01); *G16H 30/40* (2018.01); *G16H 50/20* (2018.01); *A61B 6/463* (2013.01); *G06T 2207/10081* (2013.01); *G06T 2207/10088* (2013.01); *G06T 2207/20081* (2013.01); *G06T 2207/30016* (2013.01); *G06T 2207/30104* (2013.01)

(56) References Cited

U.S. PATENT DOCUMENTS

| | | |
|---|---|---|
| 2011/0082371 A1 | 4/2011 | Chono |
| 2012/0314919 A1 | 12/2012 | Sparks et al. |
| 2018/0249979 A1* | 9/2018 | Wang .................... A61B 6/035 |
| 2019/0026888 A1* | 1/2019 | Beveridge ............. A61B 6/037 |
| 2020/0074633 A1* | 3/2020 | Fuchigami ........... A61B 5/0042 |
| 2020/0359981 A1* | 11/2020 | Straka .................. A61B 5/7275 |

OTHER PUBLICATIONS

Lee et al., "Deep into the Brain: Artificial Intelligence in Stroke Imaging," Journal of Stroke 2017;19(3):277-285 (Year: 2017).*

* cited by examiner

|  | DIFFUSION WEIGHTED IMAGE | FLAIR IMAGE | CT IMAGE |
|---|---|---|---|
| HYPERACUTE PHASE | HIGH SIGNAL | EQUAL SIGNAL | - |
| ACUTE PHASE | HIGH SIGNAL | HIGH SIGNAL | - |
| SUBACUTE PHASE | LOW SIGNAL | - | LOW SIGNAL |

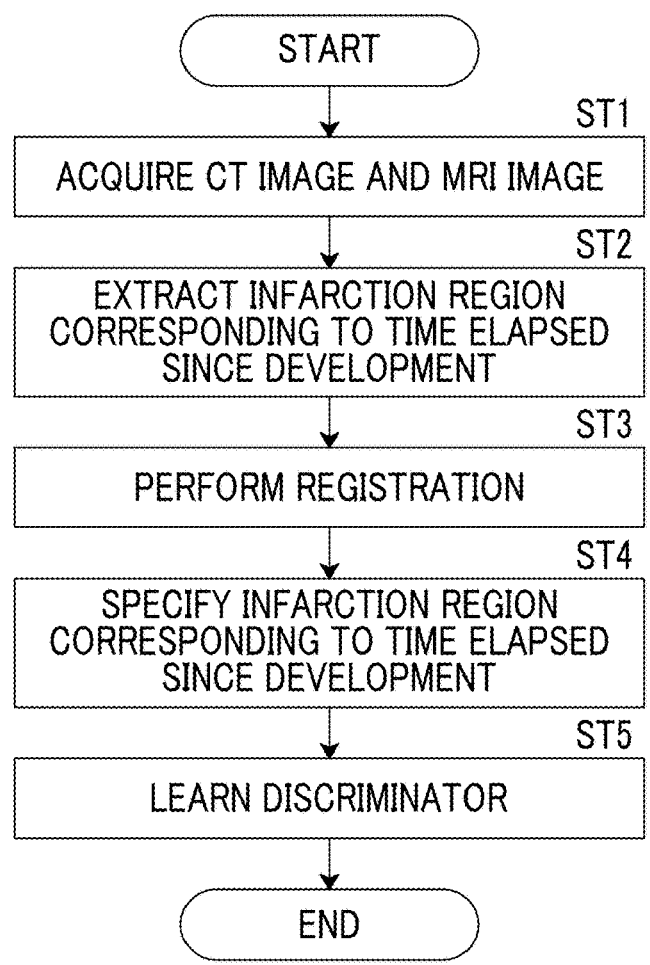
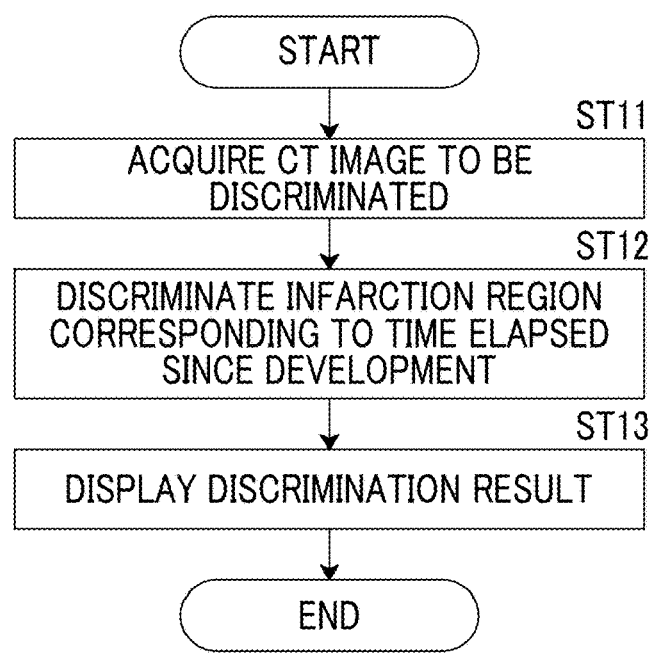

APPARATUS, METHOD, AND PROGRAM FOR LEARNING DISCRIMINATOR DISCRIMINATING INFARCTION REGION, DISCRIMINATOR FOR DISCRIMINATING INFARCTION REGION, AND APPARATUS, METHOD, AND PROGRAM FOR DISCRIMINATING INFARCTION REGION

CROSS REFERENCE TO RELATED APPLICATIONS

The present application claims priority under 35 U.S.C. § 119 to Japanese Patent Application No. 2018-162861 filed on Aug. 31, 2018. The above application is hereby expressly incorporated by reference, in its entirety, into the present application.

BACKGROUND

Technical Field

The present disclosure relates to an apparatus, method and program for learning a discriminator, a discriminator for discriminating an infarction region, and an apparatus, method, and program for discriminating an infarction region which discriminate an infarction region in a brain image according to the time elapsed since development.

Related Art

In recent years, advances in medical apparatuses, such as a computed tomography (CT) apparatus and a magnetic resonance imaging (MRI) apparatus, have made it possible to perform image diagnosis using high-resolution medical images with higher quality. In particular, in a case in which a target part is the brain, image diagnosis using, for example, CT images and MRI images makes it possible to specify regions causing cerebrovascular disorders, such as a cerebral infarction and cerebral hemorrhage. Therefore, various methods for supporting image diagnosis have been proposed.

For example, WO2009/148041 discloses a method which performs a learning operation of calculating a pattern for classifying a plurality of medical images of a living body tissue of a subject, such as ultrasound images, CT images, and MRI images, into predetermined types and storing the pattern, recognizes an input image on the basis of learning data, and displays the image. In addition, JP2013-165765A discloses a method which detects a cerebral infarction part included in an MRI diffusion weighted image (DWI), acquires, from an abnormal part of the diffusion weighted image and a diffusion weighted image of a healthy person, position conversion data required for anatomical registration therebetween, converts a single photon emission computed tomography (SPECT) image captured by a SPECT apparatus on the basis of the position conversion data such that the position of each tissue of the brain of the patient is matched with the position of each tissue of the brain of the healthy person, and discriminates the cerebral infarction part on the SPECT image. In addition, JP2014-518516A discloses a method which performs registration between a CT image and an MRI image and displays the images such that diagnosis is performed.

Thrombolytic therapy using an antiplatelet agent is performed for cerebral infarction patients. However, it has been known that the thrombolytic therapy is applied within 4.5 hours from the time when no cerebral infarction has been confirmed and the risk of bleeding after treatment becomes higher as an infarction range becomes wider over time. Therefore, it is necessary to quickly and appropriately discriminate the infarction range using medical images in order to determine whether the thrombolytic therapy is appropriate. Here, in a diffusion-weighted image, the infarction region has a signal value different from that of other regions. In particular, in the diffusion-weighted image, there is a significant difference in signal value between a cerebral infarction region in the acute phase and other regions. For this reason, in many cases, the diffusion weighted image is used to confirm the infarction region. In addition, in a case in which the time for which the thrombolytic therapy is applied has elapsed, a treatment different from the thrombolytic therapy for cerebral infarction is required. Therefore, it is also important to recognize the time elapsed since the development of cerebral infarction, such as the hyperacute phase, the acute phase, the subacute phase, and the chronic phase (old phase), using not only the MRI diffusion weighted images but also T1-weighted images, T2-weighted images, or Fluid-Attenuated Inversion Recovery (FLAIR) images, in treating cerebral infarction.

In brain diagnosis, in many cases, the presence or absence of cerebral hemorrhage is confirmed before cerebral infarction is confirmed. Since cerebral hemorrhage can be clearly confirmed in CT images, diagnosis using CT images is first performed for patients with suspected brain diseases. However, in CT images, since the difference in signal value between a cerebral infarction region in the acute phase and other regions is not so large, in many cases, it is difficult to specify infarction in the acute phase using CT images. Therefore, after diagnosis using CT images, MRI images are acquired and it is diagnosed whether cerebral infarction has developed.

However, in the configuration in which, after diagnosis using CT images, MRI images are acquired and it is diagnosed whether cerebral infarction has developed, because the time elapsed since the development of the cerebral infarction is long, the risk of bleeding after treatment with thrombolytic therapy is likely to increase. Furthermore, it is necessary to acquire a plurality of MRI images in order to recognize the time elapsed since the development of the cerebral infarction. As a result, the burden on the patient increases.

SUMMARY OF THE INVENTION

The present disclosure has been made in view of the above-mentioned problems and an object of the invention is to provide a technique that can rapidly discriminate an infarction region according to the time elapsed since the development of cerebral infarction, using CT images.

According to the present disclosure, there is provided a discriminator learning apparatus comprising: an image acquisition unit that acquires a CT image of a brain of a subject that has developed a cerebral infarction and at least one brain image of the subject acquired by a modality different from a CT apparatus which acquires the CT image; an infarction region extraction unit that extracts an infarction region corresponding to a time elapsed since the development from the brain image on the basis of at least the brain image; a registration unit that performs registration between the CT image and the brain image; an infarction region specification unit that specifies the infarction region corresponding to the time elapsed since the development in the CT image on the basis of a result of the registration; and a learning unit that learns a discriminator which discriminates an infarction region corresponding to the time elapsed since the development in an input CT image, using the infarction region corresponding to the time elapsed since the development, which has been specified in the CT image, as teacher data.

The term "on the basis of at least the brain image" includes being based on images other than the brain image, for example, CT images.

In the discriminator learning apparatus according to the present disclosure, the brain image may be an MRI image.

In the discriminator learning apparatus according to the present disclosure, the MRI image may be at least one of a diffusion weighted image, a FLAIR image, or a T2-weighted image.

According to the present disclosure, there is provided a discriminator that is learned by the discriminator learning apparatus according to the present disclosure.

According to the present disclosure, there is provided an infarction region discrimination apparatus comprising: an image acquisition unit that acquires a CT image to be discriminated; and the discriminator according to the present disclosure that discriminates an infarction region in the CT image to be discriminated according to a time elapsed since development.

The infarction region discrimination apparatus according to the present disclosure may further comprise a display control unit that displays a discrimination result of the infarction region by the discriminator on a display unit.

According to the present disclosure, there is provided a discriminator learning method comprising: acquiring a CT image of a brain of a subject that has developed a cerebral infarction and at least one brain image of the subject acquired by a modality different from a CT apparatus which acquires the CT image; extracting an infarction region corresponding to a time elapsed since the development from the brain image on the basis of at least the brain image; performing registration between the CT image and the brain image; specifying the infarction region corresponding to the time elapsed since the development in the CT image on the basis of a result of the registration; and learning a discriminator which discriminates an infarction region corresponding to the time elapsed since the development in an input CT image, using the infarction region corresponding to the time elapsed since the development, which has been specified in the CT image, as teacher data.

According to the present disclosure, there is provided an infarction region discrimination method comprising: acquiring a CT image to be discriminated; and discriminating an infarction region in the CT image to be discriminated according to a time elapsed since development, using the discriminator according to the present disclosure.

Programs that cause a computer to perform the discriminator learning method according to the present disclosure and the infarction region discrimination method according to the present disclosure may be provided.

Another discriminator learning apparatus according to the present disclosure comprises a memory that stores commands executed by a computer and a processor that is configured to execute the stored commands. The processor performs a process of acquiring a CT image of a brain of a subject that has developed a cerebral infarction and at least one brain image of the subject acquired by a modality different from a CT apparatus which acquires the CT image; a process of extracting an infarction region corresponding to a time elapsed since the development from the brain image on the basis of at least the brain image; a process of performing registration between the CT image and the brain image; a process of specifying the infarction region corresponding to the time elapsed since the development in the CT image on the basis of a result of the registration; and a process of learning a discriminator which discriminates an infarction region corresponding to the time elapsed since the development in an input CT image, using the infarction region corresponding to the time elapsed since the development, which has been specified in the CT image, as teacher data.

Another infarction region discrimination apparatus according to the present disclosure comprises a memory that stores commands executed by a computer and a processor that is configured to execute the stored commands. The processor performs a process of acquiring a CT image to be discriminated; and a process of discriminating an infarction region in the CT image to be discriminated according to a time elapsed since development, using the discriminator according to the present disclosure.

According to the present disclosure, it is possible to rapidly diagnose cerebral infarction corresponding to the time elapsed since the development of the cerebral infarction, using on CT images.

BRIEF DESCRIPTION OF THE DRAWINGS

FIG. 8 is a flowchart illustrating a process performed during learning in this embodiment.

FIG. 9 is a flowchart illustrating a process performed in a case in which the infarction region corresponding to the time elapsed since development is discriminated in this embodiment.

DETAILED DESCRIPTION

Figure 1:
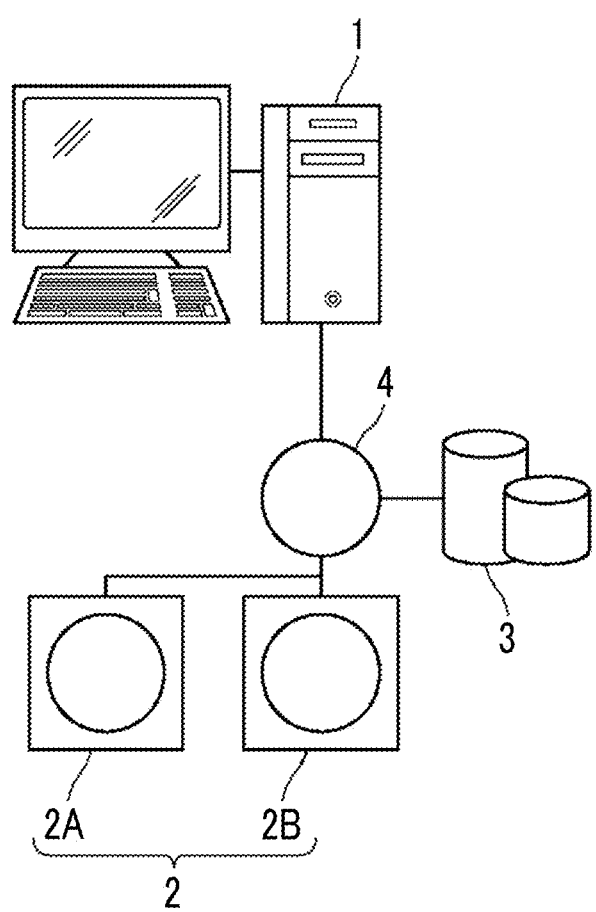
FIG. 1 is a hardware configuration diagram illustrating the outline of a diagnosis support system to which a discriminator learning apparatus, a discriminator, and an infarction region discrimination apparatus according to an embodiment of the present disclosure are applied.

Hereinafter, an embodiment of the present disclosure will be described with reference to the drawings. FIG. 1 is a hardware configuration diagram illustrating the outline of a diagnosis support system to which a discriminator learning apparatus, a discriminator, and an infarction region discrimination apparatus according to an embodiment of the present disclosure are applied. As illustrated in FIG. 1, in the diagnosis support system, an infarction region discrimination apparatus 1 according to this embodiment, a three-dimensional imaging apparatus 2, and an image storage server 3 are connected so as to communicate with each other through a network 4. The infarction region discrimination apparatus 1 includes the learning apparatus and the discriminator according to this embodiment.

The three-dimensional imaging apparatus 2 captures an image of a part of a subject to be diagnosed and generates a three-dimensional image indicating the part. The medical image generated by the three-dimensional imaging apparatus 2 is transmitted to the image storage server 3 and is then stored therein. In this embodiment, a diagnosis target part of a patient that is the subject is the brain and the three-dimensional imaging apparatus 2 includes a CT apparatus 2A and an MRI apparatus 2B. The CT apparatus 2A generates a three-dimensional CT image Bc0 including the brain of the subject and the MRI apparatus 2B generates at least one three-dimensional MRI image including the brain of the subject. In this embodiment, it is assumed that two types of images, that is, a diffusion weighted image Bm1 and a FLAIR image Bm2 are generated as the MRI images. In this embodiment, the CT image Bc0 is a non-contrast-enhanced CT image acquired by imaging without using a contrast medium. However, a contrast-enhanced CT image acquired by imaging using a contrast medium may be used. The MRI apparatus 2B is a modality different from the CT apparatus 2A. The diffusion weighted image Bm1 and the FLAIR image Bm2 are at least one brain image acquired by different modalities. In the following description, in some cases, the diffusion weighted image Bm1 and FLAIR image Bm2 are represented by MRI images Bm0.

The image storage server 3 is a computer that stores and manages various types of data and comprises a high-capacity external storage device and database management software. The image storage server 3 performs communication with other apparatuses through the wired or wireless network 4 to transmit and receive, for example, image data. Specifically, the image storage server 3 acquires various types of data including image data of the CT image and the MRI image generated by the three-dimensional imaging apparatus 2 through the network, stores the acquired data in a recording medium, such as a high-capacity external storage device, and manages the data. In addition, the storage format of the image data and the communication between the apparatuses through the network 4 are based on a protocol such as Digital Imaging and Communication in Medicine (DICOM).

The infarction region discrimination apparatus 1 is configured by installing a learning program and an infarction region discrimination program according to the present disclosure in one computer. The computer may be a workstation or a personal computer that is directly operated by a doctor who performs diagnosis or may be a server computer that is connected with them through the network. The learning program and the infarction region discrimination program are recorded on a recording medium, such as a digital versatile disc (DVD) or a compact disc read only memory (CD-ROM), and is then distributed. The learning program and the infarction region discrimination program are installed in the computer from the recording medium. Alternatively, the learning program and the infarction region discrimination program are stored in a storage device of a server computer connected to the network, or are stored in a network storage so as to be accessed from the outside, are downloaded to the computer used by the doctor on request, and are then installed in the computer.

Figure 2:
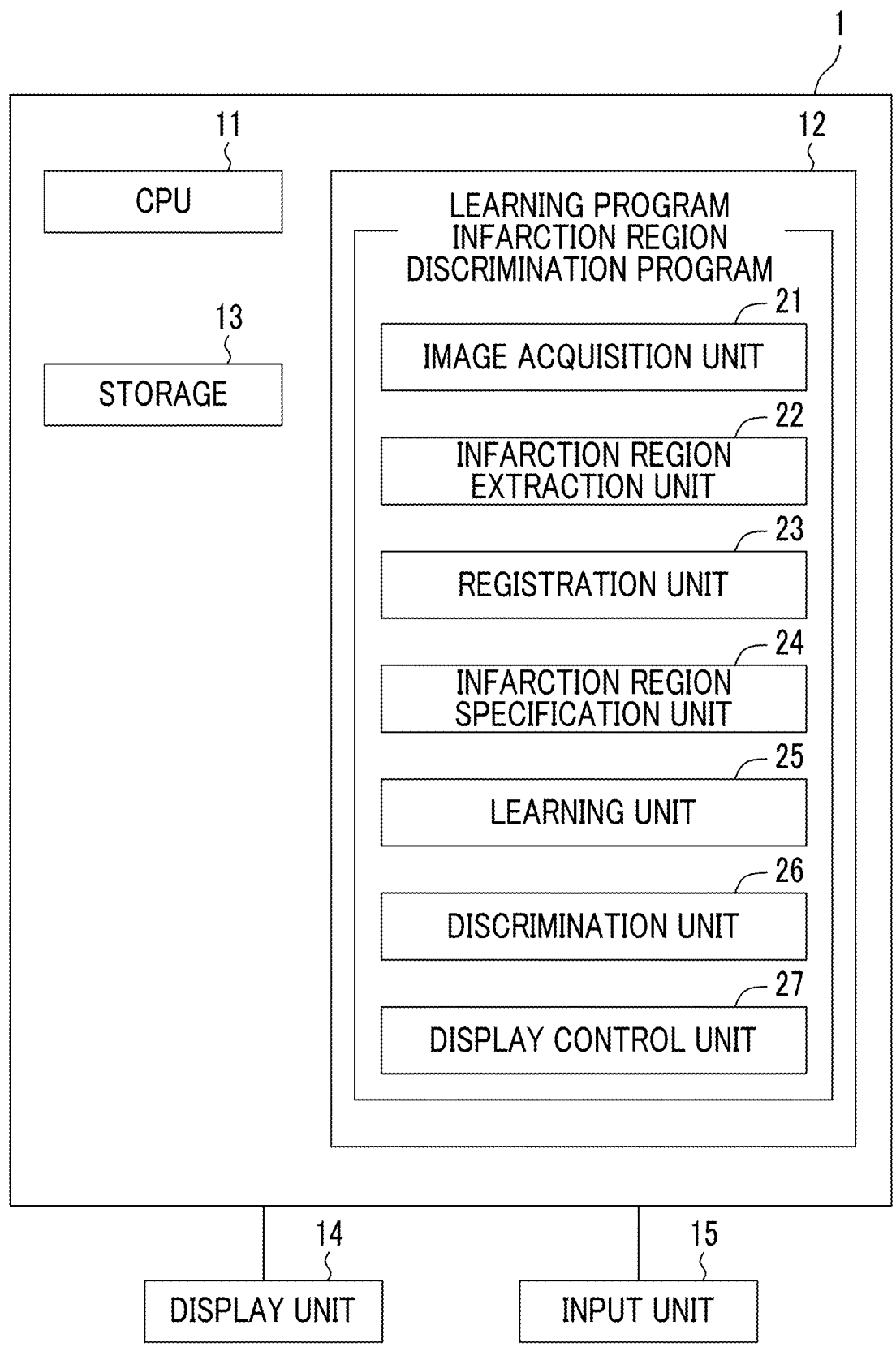
FIG. 2 is a diagram schematically illustrating the configuration of the infarction region discrimination apparatus according to this embodiment.

FIG. 2 is a diagram schematically illustrating the configuration of the infarction region discrimination apparatus according to this embodiment which is implemented by installing the learning program and the infarction region discrimination program in a computer. As illustrated in FIG. 2, the infarction region discrimination apparatus 1 has the configuration of a standard workstation and comprises a central processing unit (CPU) 11, a memory 12, and a storage 13. In addition, a display unit 14, such as a liquid crystal display, and an input unit 15 including, for example, a keyboard and a mouse are connected to the infarction region discrimination apparatus 1.

The storage 13 is, for example, a hard disk drive and stores various kinds of information including the medical images of the subject and information required for processes which have been acquired from the image storage server 3 through the network 4.

The memory 12 stores the learning program and the infarction region discrimination program. The learning program defines, as the processes performed by the CPU 11, the following processes: an image acquisition process which acquires the CT image Bc0, the diffusion-weighted image Bm1, and the FLAIR image Bm2 of the brain of the subject that has developed cerebral infarction; an infarction region extraction process which extracts an infarction region corresponding to the time elapsed since the development from the diffusion weighted image Bm1 and the FLAIR image Bm2 on the basis of at least the diffusion weighted image Bm1 and the FLAIR image Bm2; a registration process which performs registration between the CT image Bc0 and at least one of the diffusion weighted image Bm1 or the FLAIR image Bm2; an infarction region specification process which specifies the infarction region corresponding to the time elapsed since the development in the CT image Bc0 on the basis of the registration result; and a learning process which learns the discriminator for discriminating the infarction region corresponding to the time elapsed since the development in an input CT image Bc1, using the infarction region corresponding to the time elapsed since the development, which has been specified in the CT image Bc0, as teacher data. In addition, the infarction region discrimination program defines, as the processes performed by the CPU 11, the following processes: an image acquisition process which acquires the CT image Bc1 to be discriminated; a discrimination process which discriminates the infarction region corresponding to the time elapsed since the development in the CT image Bc1 to be discriminated; and a display control process which displays the discrimination result on the display unit 14.

Then, the CPU 11 performs these processes according to the programs such that the computer functions as an image acquisition unit 21, an infarction region extraction unit 22, a registration unit 23, an infarction region specification unit 24, a learning unit 25, a discriminator 26, and a display control unit 27. Here, the image acquisition unit 21, the infarction region extraction unit 22, the registration unit 23, the infarction region specification unit 24, and the learning unit 25 form the discriminator learning apparatus according to this embodiment. In addition, the discriminator 26 and the display control unit 27 form the infarction region discrimination apparatus according to this embodiment.

The image acquisition unit 21 acquires the CT image Bc0, the diffusion weighted image Bm1, and the FLAIR image Bm2 of the brain of the subject that has developed cerebral infarction from the image storage server 3 in order to learn the discriminator 26. In addition, the image acquisition unit 21 acquires the CT image Bc1 including the infarction region to be discriminated from the image storage server 3 in order to discriminate the infarction region corresponding to the time elapsed since the development. In a case in which the CT image Bc0, the CT image Bc1, the diffusion weighted image Bm1, and the FLAIR image Bm2 have been stored in the storage 13, the image acquisition unit 21 may acquire the CT image Bc0, the CT image Bc1, the diffusion weighted image Bm1, and the FLAIR image Bm2 from the storage 13. Further, the image acquisition unit 21 acquires the CT images Bc0, the diffusion weighted images Bm1, and the FLAIR images Bm2 of a large number of subjects in order to learn the discriminator 26 which will be described below.

Herein, the time elapsed since the development of an infarction region will be described. The stages of the cerebral infarction include a hyperacute phase within 24 hours after development, an acute phase for 1 to 7 days after development, a subacute phase for 1 to 4 weeks after development, and a chronic phase (old phase) after these phases. In this embodiment, it is assumed that the subacute phase and the chronic phase are collectively referred to as, for example, the subacute phase, and the hyperacute phase, the acute phase, and the subacute phase are distinguished on the basis of the time elapsed since development.

Figures 3, 4:
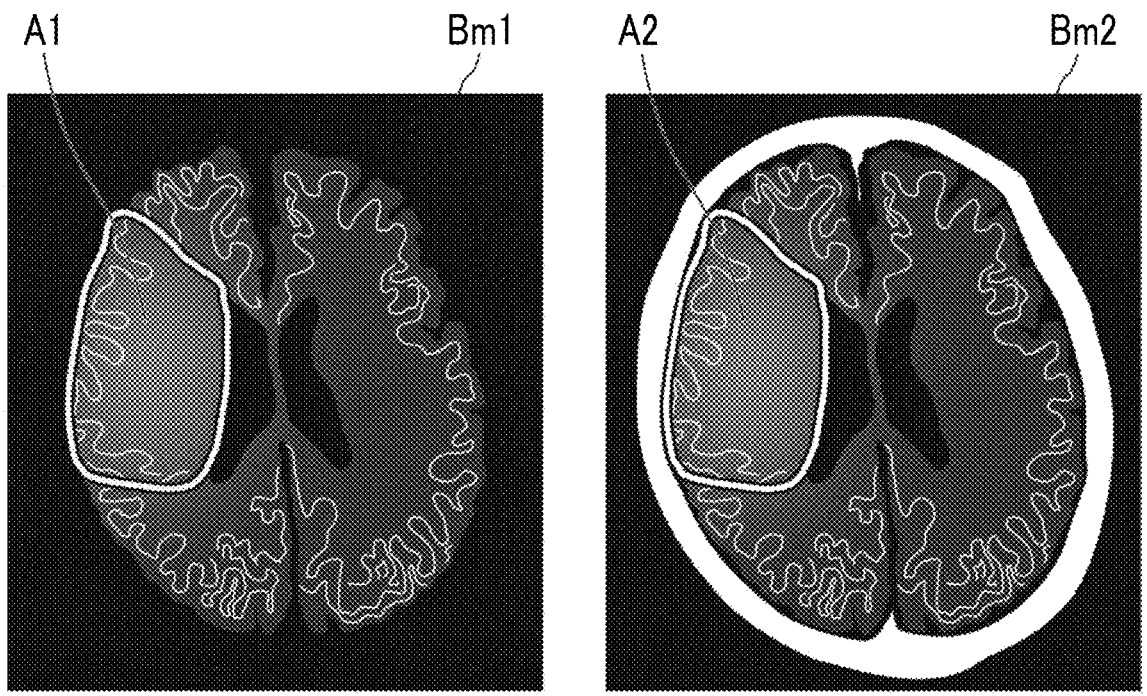
FIG. 3 is a diagram illustrating an example of a diffusion weighted image and a FLAIR image.
FIG. 4 is a diagram illustrating the relationship between signal values of a CT image, a diffusion weighted image, and a FLAIR image and the time elapsed since the development of an infarction region.

The infarction region extraction unit 22 extracts an infarction region of the brain from at least the diffusion weighted image Bm1 and the FLAIR image Bm2. In this embodiment, the infarction region is extracted also using the CT image Bc0. FIG. 3 is a diagram illustrating an example of the diffusion weighted image Bm1 and the FLAIR image Bm2. The diffusion weighted image Bm1 and the FLAIR image Bm2 are three-dimensional images. However, description will be made using a two-dimensional tomographic image in one tomographic plane of the diffusion weighted image Bm1 and the FLAIR image Bm2 for ease of understanding. As illustrated in FIG. 3, the diffusion weighted image Bm1 is an image including only the brain parenchyma from which the skull has been removed. In contrast, the FLAIR image Bm2 includes the skull. In addition, it is assumed that the diffusion weighted image Bm1 illustrated in FIG. 3 includes an infarction region in the hyperacute phase and the acute phase and the FLAIR image Bm2 includes an infarction region in the acute phase. As illustrated in FIG. 3, in the diffusion weighted image Bm1, the infarction region in the hyperacute phase and the acute phase has a higher signal value (lower density) than other regions. In the FLAIR image Bm2, the infarction region in the acute phase has a higher signal value (lower density) than other regions.

In the FLAIR image Bm2, the infarction region in the hyperacute phase has a signal value (density that is equal to or higher than) that is equal to or lower than that of other regions, which is not illustrated in FIG. 3. Further, in the diffusion-weighted image Bm1, the infarction region in, for example, the subacute phase has a signal value (density that is equal to or higher than) that is equal to or lower than that of other regions. In the CT image Bc0, the infarction region in, for example, the subacute phase has a signal value (density that is significantly higher than) that is significantly lower than that of other regions.

FIG. 4 is a diagram illustrating the relationship between the signal values of the CT image, the diffusion weighted image, and the FLAIR image and the time elapsed since the development of the infarction region. The infarction region extraction unit 22 extracts an infarction region corresponding to the time elapsed since the development on the basis of the signal values of the CT image Bc0, the diffusion weighted image Bm1, and the FLAIR image Bm2 with reference to the relationship illustrated in FIG. 4. That is, the infarction region extraction unit 22 extracts a region which has a high signal in the diffusion weighted image Bm1 and has an equal signal in the FLAIR image Bm2 as the infarction region in the hyperacute phase from at least one of the diffusion weighted image Bm1 or the FLAIR image Bm2. In addition, the infarction region extraction unit 22 extracts a region which has a high signal in the diffusion weighted image Bm1 and has a high signal in the FLAIR image Bm2 as the infarction region in the cute phase from at least one of the diffusion weighted image Bm1 or the FLAIR image Bm2. Further, the infarction region extraction unit 22 extracts a region which has a low signal in the diffusion weighted image Bm1 and has a low signal in the CT image Bc0 as the infarction region in the subacute phase from the diffusion weighted image Bm1. The relationship illustrated in FIG. 4 may be stored in the storage 13.

The infarction region extraction unit 22 may extract the infarction region corresponding to the time elapsed since the development of the disease, using the discriminator which has been learned so as to extract the infarction region corresponding to the time elapsed since the development of the disease from at least one of the diffusion weighted image Bm1 or the FLAIR image Bm2. In this case, at least one of an infarction region A1 or an infarction region A2 illustrated in FIG. 3 is extracted.

Figure 5:
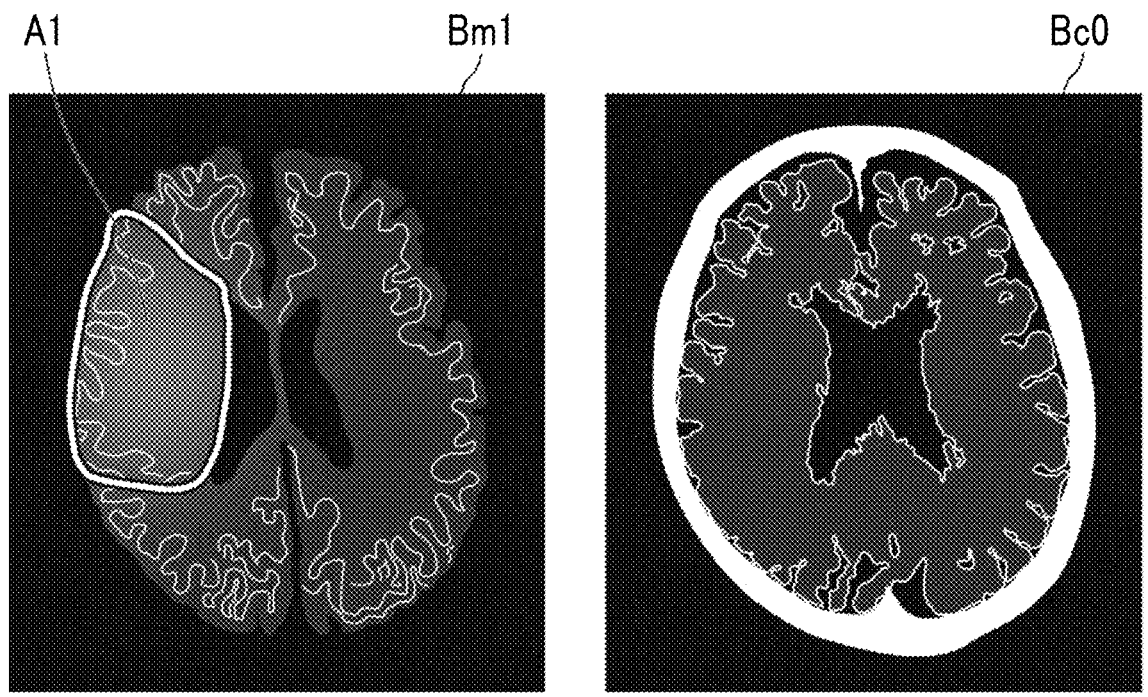
FIG. 5 is a diagram illustrating registration between the CT image and the diffusion weighted image.

The registration unit 23 performs the registration between the CT image Bc0 and at least one of the diffusion weighted image Bm1 or the FLAIR image Bm2. FIG. 5 is a diagram illustrating the registration between the CT image Bc0 and the diffusion weighted image Bm1. Both the CT image Bc0 and the diffusion weighted image Bm1 are three-dimensional images. Here, the description will be made using a two-dimensional tomographic image in one corresponding tomographic plane of the CT image Bc0 and the diffusion weighted image Bm1 for ease of understanding. As illustrated in FIG. 5, the shape of the brain is almost the same in the same subject. In the diffusion weighted image Bm1, the infarction region in the hyperacute phase and the acute phase has a higher signal value (lower density) than other regions. In contrast, in the CT image Bc0, the difference between the signal values of the infarction region in the hyperacute phase and the acute phase and other regions is not greater than that in the diffusion weighted image Bm1. The CT image Bc0 includes the skull and the brain parenchyma unlike the diffusion weighted image Bm1. Therefore, the registration unit 23 extracts a brain parenchyma region as a brain region from the CT image Bc0 and performs the registration between the extracted brain region and the diffusion weighted image Bm1.

In this embodiment, the registration unit 23 registers one of the CT image Bc0 and the diffusion weighted image Bm1 with the other, using a non-rigid registration method. In this embodiment, the CT image Bc0 is registered with the diffusion weighted image Bm1. However, the diffusion weighted image Bm1 may be registered with the CT image Bc0.

For example, a method which non-linearly converts a feature point in the CT image Bc0 into a correspondence point corresponding to a feature point in the MRI image Bm0 using a function, such as a B-spline or a thin-plate spline, can be used as the non-rigid registration method. However, the invention is not limited thereto.

In a case in which the FLAIR image Bm2 is used, the registration unit 23 performs the registration between the CT image Bc0 and the FLAIR image Bm2 similarity to the case of the diffusion weighted image Bm1.

Figure 6:
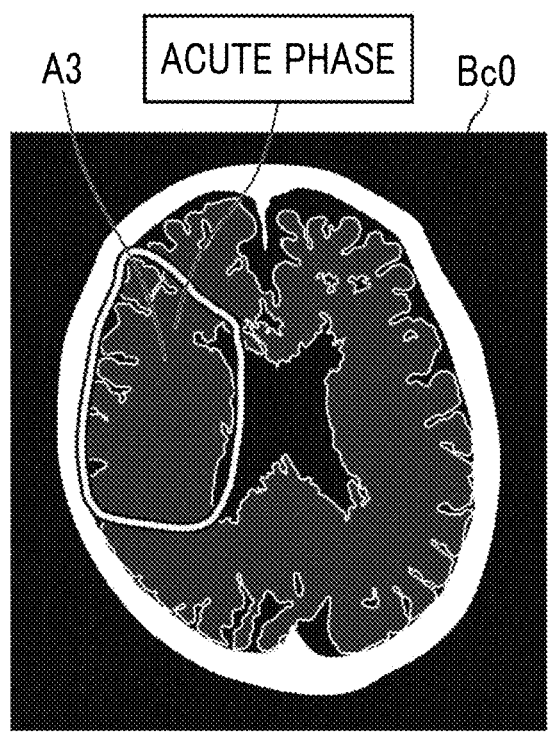
FIG. 6 is a diagram illustrating the specification of an infarction region corresponding to the time elapsed since development in the CT image.

The infarction region specification unit 24 specifies an infarction region corresponding to the time elapsed since development in the CT image Bc0 on the basis of the registration result of the registration unit 23. FIG. 6 is a diagram illustrating the specification of the infarction region corresponding to the time elapsed since the development in the CT image Bc0. As illustrated in FIG. 6, the infarction region specification unit 24 specifies, as an infarction region A3, a voxel region of the CT image Bc0 which corresponds to the infarction region A1 extracted from the MRI image Bm0 or the infarction region A2 extracted from the FLAIR image Bm2. A label corresponding to the time elapsed since the development is attached to the specified infarction region A3. FIG. 6 illustrates a state in which a label "acute stage" is attached.

The learning unit 25 learns the discriminator 26 that discriminates the infarction region corresponding to the time elapsed since the development in the input CT image, using the infarction region corresponding to the time elapsed since the development, which has been specified in the CT image Bc0, as teacher data. In this embodiment, in a case in which the CT image Bc1 to be discriminated is input, the discriminator 26 discriminates the infarction region corresponding to the time elapsed since the development in the CT image Bc1. Specifically, the discriminator 26 discriminates whether each voxel in the CT image Bc1 to be discriminated is an infarction region or a region other than the infarction region and discriminates which of one or more infarction regions corresponding to the time elapsed since the development corresponds to the infarction region in a case in which the voxel is the infarction region. Determining which of the one or more infarction regions corresponding to the time elapsed since the development corresponds to the infarction region means determining whether the infarction region is in the hyperacute phase, the acute phase, or the subacute phase. Therefore, the learning unit 25 acquires a feature amount in a region with a predetermined size (for example, 3×3) from the infarction region A3 specified in the CT images Bc0 of a plurality of subjects, inputs the acquired feature amount to the discriminator 26, and performs learning, that is, machine learning for the discriminator 26 such that the discrimination result of the infarction region corresponding to the time elapsed since the development is output.

Learning is performed in this way to generate the discriminator 26 that, in a case in which the CT image Bc1 is input, classifies the voxels of the CT image Bc1 into one or more infarction regions corresponding to the time elapsed since development and regions other than the infarction regions and discriminates the infarction region corresponding to the time elapsed since the development in the CT image Bc1 to be discriminated.

Figure 7:
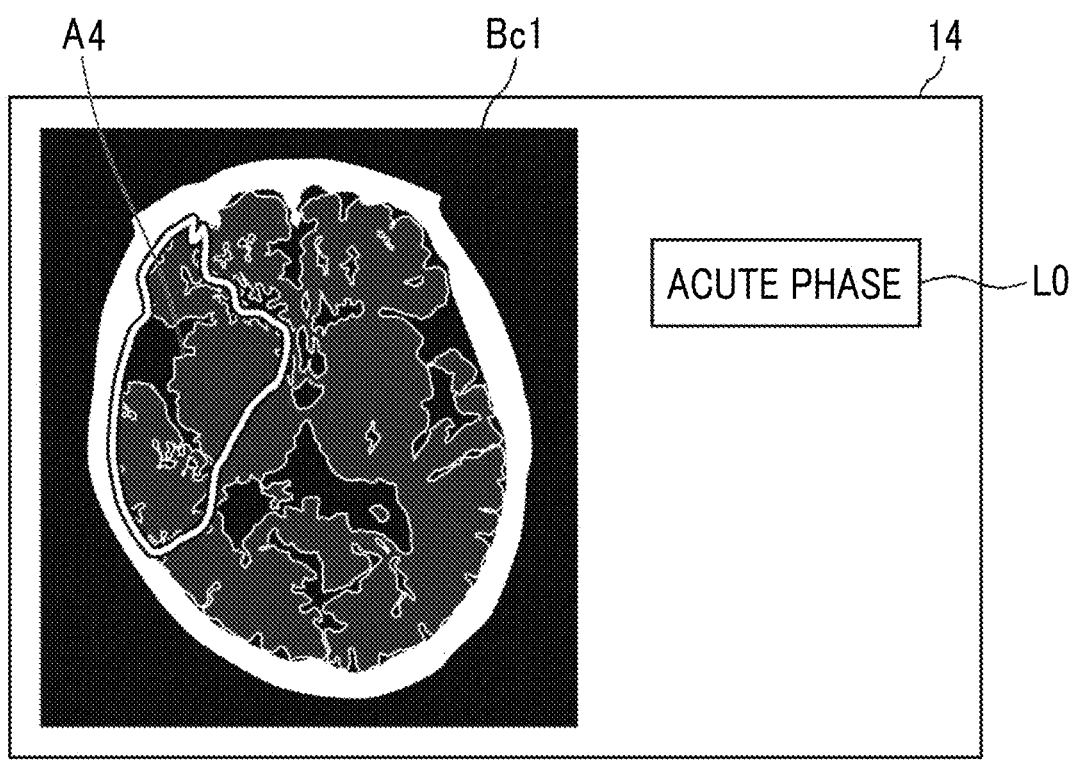
FIG. 7 is a diagram illustrating an example of the display of a discrimination result.

The display control unit 27 displays the discrimination result of the CT image Bc1 to be discriminated by the discriminator 26 on the display unit 14. FIG. 7 is a diagram illustrating an example of the display of the discrimination result. FIG. 7 illustrates a tomographic image in one tomographic plane of the CT image Bc1 to be discriminated. As illustrated in FIG. 7, in the discrimination result displayed on the display unit 14, an infarction region A4 is specified in the CT image Bc1 to be discriminated. In addition, a label L0 of "acute phase" which is the time elapsed since the development of the infarction region A4 is displayed.

For example, a support vector machine (SVM), a deep neural network (DNN), a convolutional neural network (CNN), and a recurrent neural network (RNN) can be used as the machine learning method.

Next, a process performed by this embodiment will be described. FIG. 8 is a flowchart illustrating the process performed during learning in this embodiment. First, the image acquisition unit 21 acquires the CT image Bc0 and the MRI image Bm0 (that is, the diffusion weighted image Bm1 and the FLAIR image Bm2) of the brain of the subject that has developed cerebral infarction (Step ST1). The infarction region extraction unit 22 extracts the infarction regions A1 and A2 corresponding to the time elapsed since the development from the diffusion weighted image Bm1 and the FLAIR image Bm2, respectively (Step ST2). Then, the registration unit 23 performs the registration between the CT image Bc0 and at least one of the diffusion weighted image Bm1 or the FLAIR image Bm2 (Step ST3). The infarction region specification unit 24 specifies the infarction region A3 corresponding to the time elapsed since the development in the CT image Bc0 on the basis of the registration result (Step ST4). Then, the learning unit 25 learns the discriminator 26 that discriminates the infarction region in the input CT image Bc1, using the infarction region corresponding to the time elapsed since the development, which has been specified in the CT image Bc0, as teacher data (Step ST5). Then, the process ends.

FIG. 9 is a flowchart illustrating a process performed in a case in which the infarction region corresponding to the time elapsed since the development of a disease is discriminated in this embodiment. First, the image acquisition unit 21 acquires the CT image Bc1 to be discriminated (Step ST11). The discriminator 26 discriminates the infarction region corresponding to the time elapsed since the development of the disease in the CT image to be discriminated (Step ST12). Then, the display control unit 27 displays the discrimination result on the display unit 14 (Step ST13). Then, the process ends.

As such, in this embodiment, the CT image Bc0, the diffusion weighted image Bm1, and the FLAIR image Bm2 of the brain of the subject that has developed the cerebral infarction are acquired. The infarction region corresponding to the time elapsed since the development is extracted from the diffusion weighted image Bm1 and the FLAIR image Bm2. Then, the registration between the CT image Bc0 and at least one of the diffusion weighted image Bm1 or the FLAIR image Bm2 is performed. Then, the infarction region A3 corresponding to the time elapsed since the development in the CT image Bc0 is specified on the basis of the registration result. Then, the discriminator 26 that discriminates the infarction region corresponding to the time elapsed since the development in the input CT image Bc1 is learned using the specified infarction region A1 as teacher data.

Here, since a bleeding region has a signal value that is greatly different from those of other regions in a CT image, it is easy to specify the bleeding region in the CT image. However, an infarction region has a signal value different from those of other regions in a CT image, but the difference in signal value between the infarction region and other regions is less than that between the bleeding region and other regions. In contrast, in an MRI image, the difference in signal value between the infarction region and other regions is large. In particular, since the signal value varies depending on the time elapsed since the development of a disease in the diffusion weighted image Bm1 and the FLAIR image Bm2, it is possible to specify the time elapsed since the development of the infarction region by using the CT image Bc0 in addition to the diffusion weighted image Bm1 and the FLAIR image Bm2. Therefore, in a case in which the registration between the CT image Bc0 and at least one of the diffusion weighted image Bm1 or the FLAIR image Bm2 of the brain of the subject that has developed the cerebral infarction is performed, it is possible to specify the infarction region A3 corresponding to the time elapsed since the development in the CT image Bc0 on the basis of the infarction regions A1 and A2 in the diffusion weighted image Bm1 and the FLAIR image Bm2. Then, the discriminator 26 is learned using the specified infarction region A3 corresponding to the time elapsed since the development as teacher data and the infarction region corresponding to the time elapsed since the development in the CT image Bc1 to be discriminated can be discriminated by the learned discriminator 26. Therefore, it is possible to discriminate not only a cerebral hemorrhage region but also the infarction region corresponding to the time elapsed since the development, using only the CT image. As a result, according to this embodiment, it is possible to rapidly diagnose the cerebral infarction corresponding to the time elapsed since the development of the cerebral infarction, using only the CT image.

In the above-described embodiment, the diffusion weighted image Bm1 and the FLAIR image Bm2 are used as the MRI image Bm0. However, MRI images other than the diffusion weighted image Bm1 and the FLAIR image Bm2 may be used. For example, a T1-weighted image and a T2-weighted image may be used. Further, one or more images selected from, for example, the diffusion-weighted image Bm1, the FLAIR image Bm2, the T1-weighted image, and the T2-weighted image may be used. The MRI images may be combined to specify the infarction region in the subacute phase and the infarction region in the chronic phase. Specifically, in a case in which the infarction region is equal to low signals in the diffusion weighted image Bm1 and is a high signal in the T2-weighted image, the infarction region can be specified as an infarction region in the subacute phase. In addition, in a case in which the infarction region is a low signal in the diffusion weighted image Bm1 and is a high signal in the T2-weighted image, the infarction region can be specified as an infarction region in the chronic phase. Therefore, in a case in which the discriminator 26 is learned using the above-mentioned relationship, it is possible to discriminate the infarction regions in the hyperacute phase, the acute phase, the subacute phase, and the chronic phase.

In the above-described embodiment, the CT image Bc0 is used to specify the time elapsed since the development of an infarction region. However, only the MRI image may be used.

In the above-described embodiment, the non-contrast-enhanced CT image or the contrast-enhanced CT image is used as the CT image Bc0 used to learn the discriminator 26. However, both the contrast-enhanced CT image and the non-contrast-enhanced CT image may be used to learn the discriminator 26. The use of the learned discriminator 26 makes it possible to discriminate an infarction region even in a case in which the CT image to be discriminated is any of the contrast-enhanced CT image and the non-contrast-enhanced CT image.

In the above-described embodiment, the infarction region discrimination apparatus 1 includes the learning apparatus. However, the invention is not limited thereto. That is, in the diagnosis support system, a learning apparatus that comprises the image acquisition unit 21, the infarction region extraction unit 22, the registration unit 23, the infarction region specification unit 24, and the learning unit 25 and learns the discriminator 26 may be provided separately from the infarction region discrimination apparatus 1. In this case, the infarction region discrimination apparatus 1 comprises only the image acquisition unit 21, the discriminator 26, and the display control unit 27.

In the above-described embodiment, for example, the following various processors can be used as the hardware structure of processing units performing various processes, such as the image acquisition unit 21, the infarction region extraction unit 22, the registration unit 23, the infarction region specification unit 24, the learning unit 25, the discriminator 26, and the display control unit 27. The various processors include a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

What is claimed is:

1. A learning apparatus comprising at least one processor, wherein the processor is configured to:
   acquire a CT image of a brain of a subject that has developed a cerebral infarction and at least one brain image of the subject acquired by a modality different from a CT apparatus which acquires the CT image;
   extract a first infarction region from the brain image, corresponding to a time elapsed since the subject has developed the cerebral infarction and based on at least the brain image;
   perform registration between the CT image and the brain image;
   specify a second infarction region in the CT image, corresponding to the time elapsed since the subject has developed the cerebral infarction and based on a result of the registration; and
   learn a discriminator which discriminates a third infarction region corresponding to the time elapsed since the subject has developed the cerebral infarction in an input CT image, using the second infarction region corresponding to the time elapsed since the subject has developed the cerebral infarction, which has been specified in the CT image, as teacher data.

2. The learning apparatus according to claim 1, wherein the brain image is an MRI image.

3. The learning apparatus according to claim 2, wherein the MRI image is at least one of a diffusion weighted image, a FLAIR image, or a T2-weighted image.

4. A discriminator that is learned by the learning apparatus according to claim 1.

5. An infarction region discrimination apparatus comprising at least one processor, wherein the processor is configured to:
acquire a CT image to be discriminated; and
the discriminator according to claim 4 that discriminates the third infarction region in the CT image to be discriminated according to the time elapsed since the subject has developed the cerebral infarction.

6. The infarction region discrimination apparatus according to claim 5, wherein the processor is further configured to:
display a discrimination result of the third infarction region by the discriminator on a display.

7. A learning method comprising:
acquiring a CT image of a brain of a subject that has developed a cerebral infarction and at least one brain image of the subject acquired by a modality different from a CT apparatus which acquires the CT image;
extracting a first infarction region from the brain image, corresponding to a time elapsed since the subject has developed the cerebral infarction and based on at least the brain image;
performing registration between the CT image and the brain image;
specifying a second infarction region in the CT image, corresponding to the time elapsed since the subject has developed the cerebral infarction and based on a result of the registration; and
learning a discriminator which discriminates a third infarction region corresponding to the time elapsed since the subject has developed the cerebral infarction in an input CT image, using the second infarction region corresponding to the time elapsed since the subject has developed the cerebral infarction, which has been specified in the CT image, as teacher data.

8. An infarction region discrimination method comprising:
acquiring the CT image to be discriminated; and
discriminating the third infarction region in the CT image to be discriminated according to the time elapsed since the subject has developed the cerebral infarction, using the discriminator according to claim 4.

9. A non-transitory computer-readable storage medium that stores a learning program that causes a computer to perform:
acquiring a CT image of a brain of a subject that has developed a cerebral infarction and at least one brain image of the subject acquired by a modality different from a CT apparatus which acquires the CT image;
extracting a first infarction region from the brain image, corresponding to a time elapsed since the subject has developed the cerebral infarction and based on at least the brain image;
performing registration between the CT image and the brain image;
specifying a second infarction region in the CT image, corresponding to the time elapsed since the subject has developed the cerebral infarction and based on a result of the registration; and
learning a discriminator which discriminates third infarction region corresponding to the time elapsed since the subject has developed the cerebral infarction in an input CT image, using the second infarction region corresponding to the time elapsed since the subject has developed the cerebral infarction, which has been specified in the CT image, as teacher data.

10. A non-transitory computer-readable storage medium that stores an infarction region discrimination program that causes a computer to perform:
acquiring the CT image to be discriminated; and
discriminating the third infarction region in the CT image to be discriminated according to the time elapsed since the subject has developed the cerebral infarction, using the discriminator according to claim 4.

* * * * *